United States Patent [19]

van de Moesdijk et al.

[11] Patent Number: 4,667,034

[45] Date of Patent: May 19, 1987

[54] PROCESS FOR THE PREPARATION OF A 2-ALKYLPYRIMIDINE

[75] Inventors: Cornelis G. M. van de Moesdijk, Spaubeek; Hubertus J. A. V. Delahaye, Voerendaal; Antonius J. J. M. Teunissen, Geleen, all of Netherlands

[73] Assignee: Stamicarbon B.V., Geleen, Netherlands

[21] Appl. No.: 839,733

[22] Filed: Feb. 14, 1986

[30] Foreign Application Priority Data

Feb. 15, 1985 [NL] Netherlands ..................... 8500431
Oct. 12, 1985 [NL] Netherlands ..................... 8502797

[51] Int. Cl.$^4$ .......................................... C07D 239/26
[52] U.S. Cl. .......................................... 544/242
[58] Field of Search ..................................... 544/242

[56] References Cited

U.S. PATENT DOCUMENTS 4,127,652 11/1978 Maurer et al. ..................... 514/86
4,376,201 3/1983 Pews ..................... 544/242
4,493,929 1/1985 Pews ..................... 544/242

FOREIGN PATENT DOCUMENTS 0117882 3/1983 European Pat. Off. .

*Primary Examiner*—Joseph Paul Brust
*Attorney, Agent, or Firm*—Cushman, Darby & Cushman

[57] ABSTRACT

The process according to the invention for the preparation of a 2-propyl- or 2-butylpyrimidine, in which the corresponding 2-alkyl-1,4,5,6-tetrahydropyrimidine is dehydrogenated in the gas phase with a palladium-containing catalyst and in which a 2-propyl- or 2-butylpyrimidine is recovered from the reaction mixture, is characterized in that the gas-phase reaction is carried out using a carbon monoxide-hydrogen reactant. As this is understood a mixture of carbon monoxide and hydrogen and/or a compound capable of at least partial decomposing into CO and $H_2$ under the reaction conditions.

9 Claims, No Drawings

PROCESS FOR THE PREPARATION OF A 2-ALKYLPYRIMIDINE

The invention relates to a process of a 2-propyl- or 2-butylpyrimidine in which the corresponding 2-alkyl-1,4,5,6-tetrahydropyrimidine is dehydrogenated in the gas phase with a noble metal containing catalyst and in which a 2-propyl- or 2-butylpyrimidine is recovered from the reaction mixture.

Such a process is described in EP-A-117882 for isopropyl or t-butyl as the alkyl group. According to EP-A-117882, these 2-alkyltetrahydropyrimidines are dehydrogenated in the absence of hydrogen and water, the yield being 58–86% for 2-t-butylpyrimidine and 73–86% for 2-isopropylpyrimidine. These yields were measured during experiments lasting at most 3 hours.

For a route to be commercially attractive, the catalyst to be used must have a long service life and the yield must remain constant with time. Applicant has found that the process described above does not meet these requirements. The process according to EP-A-117882 results in rapid deterioration of the catalyst performance. The invention provides a solution to this problem.

The process according to the invention for the preparation of a 2-propyl- or 2-butylpyrimidine, in which the corresponding 2-alkyl-1,4,5,6-tetrahydropyrimidine is dehydrogenated in the gas phase with a palladium-containing catalyst and in which a 2-propyl- or 2-butylpyrimidine is recovered from the reaction mixture, is characterized in that the gas-phase reaction is carried out using a carbon monoxide-hydrogen reactant. As this is understood a mixture of carbon monoxide and hydrogen and/or a compound capable of at least partial decomposing into CO and $H_2$ under the reaction conditions.

Surprisingly, it has been found that application of a compound that decomposes into carbon monoxide and hydrogen, or application of these components themselves or of a combination thereof, results in a prolonged use of the catalyst. This is all the more surprising since carbon monoxide is known to be a strong catalyst poison for noble metals.

As starting materials for the dehydrogenation, all 2-butyl- and 2-propyl-1,4,5,6-tetrahydropyrimidines can be applied, such as 2-n-propyl-, 2-i-propyl-, 2-i-butyl-, 2-n-butyl-, n-butyl- and 2-t-butyl-1,4,5,6-tetrahydropyrimidine.

2-Alkylpyrimidines or the amides can, for instance, be prepared as described in EP-A-0117882.

The process according to the invention is preferably carried out at a temperature between 250° and 400° C., the 2-alkylpyrimidine yield then being highest.

As carbon monoxide-hydrogen reactant, use can be made, for instance, of alcohols such as methanol, ethanol and higher alcohols. Besides the carbon monoxide-hydrogen reactant, also an inert gas, such as nitrogen or helium, can be passed through the reactor to achieve uniform evaporation of the starting mixture.

Application of methanol and/or ethanol on the one hand has the advantage that uniform evaporation of the starting mixture is ensured, while on the other hand it is advantageous that under the reaction conditions a portion thereof decomposes into a carbon monoxide and hydrogen in a ratio that is favourable to the reaction. It further is advantageous that the starting compound is well soluble in the alcohol used, so that the starting compounds can in a simple manner be converted to the gas phase.

The molar amount of the carbon monoxide-hydrogen reactant, calculated as the total of CO and $H_2$, generally is 0.5–100, by preference 2–50 times the amount of 2-alkyl-1,4,5,6-tetrahydropyrimidine to be converted. If the amount of carbon monoxide-hydrogen reactant is smaller than a 2-fold molar excess, the 2-alkylpyrimidine yield decreases. Amounts larger than a 50-fold molar excess do not offer any additional advantage, but they do require a relatively large reactor volume, which adversely affects the fixed costs of the process. The $CO:H_2$ ratio is not very critical and may, for instance, vary from 1:10 to 10:1.

In the process according to the invention, palladium-containing catalysts are used. These catalysts generally contain 0.1–10 wt.% palladium, by preference 0.5–5 wt.%, calculated on the total catalyst. An alkali metal can also be added to the catalyst, in amounts between 0.1 and 2 wt.%, calculated on the total catalyst.

The catalyst can be applied on known carriers. Such carriers may contain, for instance, aluminium oxide, carbon and silicon oxide. Aluminumoxide is preferred as a carrier, because very good results are achieved.

Preferably, the catalyst is alkalimetal promoted, because in that case the life-time of the catalyst-performance is increased.

Catalysts as described above usually are commercially available.

For practical realization of the process according to the invention, the embodiments known per se of gas-phase reactions can be used, for instance the embodiment in which the gaseous starting mixture is passed over the catalyst in the form of a solid bed or a so-called fluid bed. The space velocity may be varied, for instance between 0.001 and 2 g starting compound per milliliter catalyst material (bulk volume) per hour. The pressure at which the gas-phase reaction takes place in itself is not important, so that the reaction will generally be performed at autogeneous pressure. Of course, the pressures and temperatures chosen must be such that there will be no appreciable condensation of any of the products in or on the catalyst.

Working up of the 2-alkylpyrimidine obtained in the reaction can take place in a manner known per se by cooling followed by, for instance, distillation or extraction.

2-Alkylpyrimidines are used as precursors of crop protection agents such as O-alkyl-O[pyrimidine(5)yl]-(thiono)-(thiol)-phosphate(phosphonate)acid esters or ester amides, as described in U.S. Pat. No. 4,127,652.

The invention will be elucidated in the following examples.

EXAMPLE 1

A 27 wt.% solution of 2-t-butyl-1,4,5,6-tetrahydropyrimidine in methanol was introduced into the top of a metal film evaporator at a rate of 41 g/h. The evaporator temperature was kept at 270° C. An additional stream of $H_2$ was introduced, at a flow rate of 6 Nl/h (Nl meaning normal liters), into the evaporator bottom to entrain the vapour over the catalyst.

The reactor consists of a glass or metal tube of 400 mm length and 2.54 mm internal diameter. It contained 50 g catalyst. The catalyst was 1 wt.% Pd + 1 wt.% Na on $\gamma$-$Al_2O_3$.

The reactor was fully enclosed in a thermostated environment which was kept at 340° C. Depending on the methanol decomposition in the top of the catalyst bed, a bed temperature was measured that was 10°–50° C. higher than the bath temperature. The reaction gases were condensed in two stages. In the first stage, cooling was effected in a condenser with cooling water of 10° C., while in the second stage the off-gases were passed through a glass filter, which was scrubbed with 20 g/h methanol. The amount of off-gas was measured with a soap film flow meter and the composition was determined by GLC analysis. Besides large amounts of CO and $H_2$, small amounts of $CO_2$ were found. The 2-t-butylpyrimidine and methanol were collected during two-hour periods and analyzed by various GLC methods (incl. a 30 mm column with carbowax/KOH).

Table 1 presents the 2-t-butylpyrimidine yield as a function of time. It also gives the amounts of off-gas and the CO concentrations of the off-gas as a measure of methanol decomposition. The yield is defined as the number of moles 2-t-butylpyrimidine analyzed divided by the number of moles 2-t-butyl-1,4,5,6-tetrahydropyrimidine supplied in the same period (molar yield).

TABLE 1

| Operating time before sampling in hours | 2-t-butylpyrimidine yield % | conversion % | CO content of off-gas % |
|---|---|---|---|
| 8 | 85 | 99.8 | 25.8 |
| 20 | 86 | 99.9 | 23.1 |
| 44 | 87 | 100 | 23.0 |
| 70 | 88 | 100 | 22.1 |
| 94 | 89 | 100 | 22.0 |
| 110 | 90 | 100 | — |
| 134 | 91 | 100 | — |
| 180 | 90 | 100 | — |
| 220 | 89 | 99.9 | 20.5 |
| 270 | 89 | 100 | 20.4 |

COMPARATIVE EXPERIMENT A

A 27 wt.% solution of 2-t-butyl-1,4,5,6-tetrahydropyrimidine in pyridine (instead of methanol) was passed over a fresh catalyst, identical with that of Example I, at a flow rate of 41 g/h, in a manner otherwise analogous to that of Example I.

Table 2 gives the 2-t-butylpyrimidine yields versus time.

Table 2

| Operating time before sampling, in hours | 2-t-butylpyrimidine yield % | conversion % |
|---|---|---|
| 8 | 83 | 99.8 |
| 44 | 78 | 100 |
| 94 | 65 | 99.8 |
| 120 | 58 | 95.0 |
| 160 | 50 | 82 |

COMPARATIVE EXPERIMENT B

Using the same procedure as in Example I, a 27 wt.% solution of 2-t-butyl-1,4,5,6-tetrahydropyrimidine in pyridine was passed over a 50 g of a 0.5 wt.% Pd/α-$Al_2O_3$ catalyst at a flow rate of 41 g/h. The results are shown in Table 3.

TABLE 3

| Operating time before sampling, in hours | 2-t-butylpyrimidine yield % | conversion % |
|---|---|---|
| 2 | 83 | 100 |
| 4 | 55 | 95.0 |
| 8 | 25 | 42.5 |
| 20 | 5 | 35.1 |

COMPARATIVE EXPERIMENT C 2-t-butyl-1,4,5,6-tetrahydropyrimidine was melted and charged to a reactor as in Example I, provided with 50 g 0.5 wt.% palladium on α-alumina, the flow rate being about 15 g/h the catalyst bed temperature was 200°–325° C.

After 190 g had been added, the 2-t-butylpyrimidine yield was 80%, while the next 190 g yielded only 58 wt.%. After 16 hours, conversion had dropped to 38% and the yield to 7%.

EXAMPLES II AND III

Experiments further analogous to that of Example I were conducted using other molar ratios between 2-t-butyl-1,4,5,6-tetrahydropyrimidine and methanol.

In one experiment, a 35 wt.% solution (example II) of 2-t-butyl-1,4,5,6-tetrahydropyrimidine in methanol was used at a flow rate of 32 g/h, while in another a 50 wt.% solution (example III) of 2-t-butyl-1,4-5,6-tetrahydropyrimidine in methanol was fed at 22 g/h. In both experiments, the load as regards the pyrimidine component was the same as in Example I.

Table 4 summarizes the results obtained on samples taken at different points of time.

TABLE 4

| Time before sampling, in hours | 2-t-butylpyrimidine, % | conversion, % |
|---|---|---|
| II. 35% methanol solution | | |
| 20 | 86 | 99.8 |
| 60 | 87 | 100 |
| 125 | 88 | 100 |
| III. 50% methanol solution | | |
| 20 | 83 | 99.8 |
| 60 | 85 | 100 |
| 125 | 85 | 100 |

EXAMPLE IV

Solutions of 10 wt.%, 15 wt.% and 20 wt.% 2-t-butyl-1,4,5,6-tetrahydropyrimidine in methanol were passed over a 1% Pd+1% Na on γ-$Al_2O_3$ catalyst at flow rates of 100 g/h, 70 g/h and 50 g/h, respectively.

After 80 hours, t-butylpyrimidine yields of 85, 83 and 87%, respectively were measured.

EXAMPLE V

In an analogous manner to that of Example IV, a solution of 20 wt.% 2-t-butyl-1,4,5,6-tetrahydropyrimidine in ethanol was passed, to the reactor at a flow rate of 50 g/h, via the evaporator over the catalyst, use being made of 12 NL/h $H_2$. The off-gas was found to contain $CH_4$ and traces of CO and $H_2$. Ethanol conversion to CO, $H_2$ and $CH_4$ amounted to 30–40%.

Analogous to Example I, the 2-t-butylpyrimidine yield and the 2-t-butyl-1,4,5,6-tetrahydropyrimidine conversion were measured as a function of time.

In Table 5, some of the values found are given.

TABLE 5

| Time, hours | 2-t-butylpyrimidine yield, % | conversion, % |
|---|---|---|
| 24 | 87 | 100 |

TABLE 5-continued

| Time, hours | 2-t-butylpyrimidine yield, % | conversion, % |
| --- | --- | --- |
| 40 | 86 | 100 |
| 80 | 87 | 100 |
| 120 | 86 | 99.5 |

EXAMPLES VI-IX AND COMPARATIVE EXPERIMENT D

In four experiments and in comparative experiment D, a hot (60° C.) solution of 20 wt.% 2-t-butyl-1,4,5,6-tetrahydropyrimidine in 2-t-butylpyrimidine (purity>99.9%) was pumped to a film evaporator set at 270° C.

Whereas in comparative experiment D exclusively $H_2$ was metered, in the four other experiments an $H_2/CO$ mixture was added as the carbonmonoxide-hydrogen reactant.

Further the experiments were performed analogous to experiment I.

The solution was fed to the evaporator at a rate of 50 g/h, while the temperature of the heating medium was set at 340° C. Per hour, 50 Nl of gas was supplied to the evaporator.

After 60 and 80 hours, all product was condensed during a four-hour period, following which it was weighed and analyzed for its 2-t-butylpyrimidine content. Table 6 gives the 2-t-butylpyrimidine yields on the basis of the amounts of 2-t-butyl-1,4,5,6-tetrahydropyrimidine supplied in the same period of time.

TABLE 6

| Exp. | D | VI | VII | VIII | IX |
| --- | --- | --- | --- | --- | --- |
| gas feed $H_2$ Nl/h | 25 | 22.5 | 15 | 10 | 7 |
| CO | | 2.5 | 10 | 15 | 18 |
| conversion (%) | 65 | 87 | 90 | 90 | 87 |
| yield (%) | 85 | 100 | 100 | 100 | 100 |
| After 60 hours | | | | | |
| conversion (%) | 59 | 85 | 89 | 90 | 88 |
| yield (%) | 70 | 98 | 100 | 100 | 100 |
| After 80 hours | | | | | |

EXAMPLE IX

Pure 2-t-butyl-1,4,5,6-tetrahydropyrimidine was heated at about 150° C. to above its melting point and pumped into the top of a film evaporator kept at a temperature of 280° C., further this experiment was performed analogous to example VI.

At the bottom of the film evaporator, a mixture of $H_2$ and carbon monoxide was introduced, which entrained the tetrahydropyrimidine over the catalyst bed. The temperature of the bath surrounding the reactor was 320° C., and the same temperature was measured in the catalyst bed.

Table 7 presents the yield of various experiments.

The samples were taken 80 hours after the start of each experiment.

TABLE 7

| gas feed, Nl/h | CO, % | load, grams per ml catalyst per hour | 2-t-butyl-pyrimidine yield % | conversion, % |
| --- | --- | --- | --- | --- |
| 40 | 30 | 0.2 | 88 | 100 |
| 60 | 30 | 0.2 | 89 | 100 |
| 40 | 15 | 0.2 | 85 | 100 |
| 80 | 30 | 0.45 | 89 | 100 |

EXAMPLE XI

In a manner analogous to that of Example I, experiments were conducted in which catalyst temperature and load varied per experiment. In all experiments a 27 wt.% solution in methanol was applied, while LHSV is defined as g t-butyl-1,4,5,6-tetrahydropyrimidine per hour, metered per g catalyst.

The reactor contained 50 g fresh 1 wt.% Pd + 1 wt.% Na/γ-Al$_2$O$_3$ catalyst.

For comparison purposes, the results given in Table 8 include the 2-t-butylpyrimidine yields after 80 and 120 hours.

TABLE 8

| Temp., °C. | LHSV h$^{-1}$ | yield, % | | conversion, % | |
| --- | --- | --- | --- | --- | --- |
| | | 80 h | 120 h | 80 h | 120 h |
| 300 | 0.18 | 88 | 89 | 100 | 100 |
| 320 | 0.18 | 91 | 91 | 100 | 100 |
| 320 | 0.30 | 91 | 91 | 100 | 100 |
| 320 | 0.40 | 90 | 90 | 100 | 100 |
| 320 | 0.55 | 88 | 86 | 98 | 97 |
| 320 | 1.10 | 82 | 78 | 91 | 87 |
| 280 | 0.22 | 87 | 85 | 98 | 97 |
| 350 | 0.22 | 89 | 90 | 100 | 100 |
| 370 | 0.22 | 89 | 88 | 100 | 100 |

EXAMPLE XI

Analogous to Example I, instead of 2-t-butyl-1,4,5,6-tetrahydropyrimidine, 2-n-propyl-1,4,5,6-tetrahydropyrimidine in a 25 wt.% solution in methanol was passed over an identical catalyst (50 g). The catalyst contained 1 wt.% Pd and 1 wt.% Na on γ-Al$_2$O$_3$.

The temperature of the heating medium surrounding the entire reactor tube was 320° C. The rate of evaporation amounted to 45 g/h.

From analysis of the reaction product, after condensation in two stages, it appeared that the 2-n-propylpyrimidine yields vs. time were virtually the same as those when preparing 2-t-butylpyrimidine according to the invention.

The overall yield of the 200-hour experiment was 85%.

EXAMPLE XIII

In a 100-hour experiment with 2-isopropyl-1,4,5,6-tetrahydropyrimidine, conducted fully analogously to Example XI, a 2-isopropylpyrimidine yield of 88% was realized.

EXAMPLE XIV

In a 100-hour experiment with 2-n-butyl-1,4,5,6-tetrahydropyrimidine, likewise conducted fully analogously to Example XII, a 2-n-butylpyrimidine yield of 81% was achieved.

EXAMPLE XV-XIX

In some experiments, analogous to that of Example I, the Pd and Na content of the catalyst was varied. The results are shown in Table 9.

TABLE 9

| | catalyst in wt. % | yield after 80 hours, % | conversion, % |
| --- | --- | --- | --- |
| XV | 1% Pd + 1% Na/γAl$_2$O$_3$ | 89 | 100 |
| XVI | 1% Pd + 0.5% Na/γAl$_2$O$_3$ | 85 | 100 |
| XVII | 2% Pd + 1% Na/γAl$_2$O$_3$ | 91 | 100 |

Instead of Na, also an other alkalimetal, in further analogous ways,

TABLE 9-continued

| catalyst in wt. % | | yield after 80 hours, % | conversion, % |
|---|---|---|---|
| can be used, as is evident from the following data: | | | |
| XVIII | 1% Pd + 0.4% Li/$\gamma$Al$_2$O$_3$ | 79 | 100 |
| XIX | 1% Pd + 1.8% K/$\gamma$Al$_2$O$_3$ | 73 | 100 |

We claim:

1. A process for the catalytic dehydrogenation of a 2-alkyl-1,4,5,6-tetrahydropyrimidine to form the corresponding 2-alkylpyrimidine, which consists essentially in dehydrogenating a 2-alkyl-1,4,5,6-tetrahydropyrimidine, wherein said alkyl is selected from the group consisting of 2-n-butyl-, 2-sec-butyl-, 2-i-butyl-, 2-t-butyl, 2-n-propyl- and 2-isopropyl-alkyl radicals, in a gas phase reaction at a temperature between 250° and 400° C. over a catalyst comprising from 0.1 to 10 wt.% palladium deposited on a carrier wherein said gas phase reaction is supplied with a source of carbon monoxide and hydrogen such that the total molar amount of CO and H$_2$ is from 0.5 to 100 times the molar amount of said pyrimidine.

2. Process according to claim 1, wherein per unit time the total number of moles of carbon monoxide and hydrogen supplied to the reaction is 2–50 times the number of moles of the 2-alkyltetrahydropyrimidine supplied.

3. Process according to claim 1, wherein said source of carbon monoxide and hydrogen is selected from the group consisting of methanol and ethanol.

4. Process according to claim 1, wherein said catalyst contains 0.5–5 wt.% palladium calculated on the basis of the total weight of the catalyst.

5. Process according to claim 4, wherein said catalyst contains, 0.1–2 wt.% of an alkali metal, calculated on the basis of the total weight of the catalyst.

6. Process according to claim 4, wherein the catalyst comprises an alumina support.

7. Process according to claim 1, wherein said source of carbon monoxide and hydrogen is selected from the group consisting of a mixture of carbon monoxide and hydrogen and compounds capable of at least partially decomposing into carbon monoxide and hydrogen at a temperature between 250° and 400° C.

8. A process for the catalytic dehydrogenation of a 2-alkyl-1,4,5,6-tetrahydropyrimidine to form the corresponding 2-alkylpyrimidine, which consists essentially in dehydrogenating a 2-alkyl-1,4,5,6-tetrahydropyrimidine, wherein said alkyl is selected from a group consisting of 2-n-butyl-, 2-sec-butyl-, 2-i-butyl-, 2-t-butyl-, 2-n-propyl- and 2-isopropyl-alkyl radicals in a gas phase reaction at a temperature between 250° and 400° C. over a catalyst containing 0.5–5 wt.% palladium and 0.1–2 wt.% of an alkali metal, calculated on the basis of the total weight of the catalyst, wherein said gas phase reaction is supplied with a source of carbon monoxide and hydrogen selected from the group consisting of methanol and ethanol, such that the total molar amount of CO and H$_2$ is from 0.5 to 100 times the molar amount of said pyrimidine.

9. A process according to claim 8, wherein the total molar amount of CO and H$_2$ is from 2 to 50 times the molar amount of said pyrimidine.

* * * * *